United States Patent [19]

Winer

[11] Patent Number: 5,417,326
[45] Date of Patent: May 23, 1995

[54] SYRINGE CONTAINER

[76] Inventor: Donald B. Winer, Three Middle Rd., Stuart, Fla. 34996

[21] Appl. No.: 220,987

[22] Filed: Mar. 31, 1994

[51] Int. Cl.⁶ .............................................. B65D 85/30
[52] U.S. Cl. ..................... 206/365; 220/288; 220/296; 604/192; 604/198
[58] Field of Search ............... 206/365, 364; 604/192, 604/198; 220/288, 296, 297, 300

[56] References Cited

U.S. PATENT DOCUMENTS

| | | |
|---|---|---|
| 405,100 | 6/1889 | Kloppe . |
| 764,564 | 7/1904 | Dreyer . |
| 1,378,806 | 5/1921 | Ausubel . |
| 1,711,594 | 5/1929 | Gillespie ............................ 206/365 |
| 1,838,825 | 12/1931 | Goldstein ........................ 206/365 X |
| 3,244,272 | 4/1966 | Beaman et al. ................. 220/288 X |
| 3,342,319 | 9/1967 | Faulseit ............................ 206/365 |
| 3,434,587 | 3/1969 | Ciampa ............................ 206/365 |
| 3,677,247 | 7/1972 | Brown . |
| 3,783,997 | 1/1974 | Brown . |
| 3,890,971 | 6/1975 | Leeson et al. ................... 202/365 X |
| 3,930,499 | 1/1976 | Rimbaud . |
| 3,943,927 | 3/1976 | Norgren . |
| 3,993,063 | 11/1976 | Larrabee . |
| 4,334,536 | 6/1982 | Pfleger . |
| 4,573,973 | 3/1986 | Mezi . |
| 5,019,051 | 5/1991 | Hake . |
| 5,074,848 | 12/1991 | Burt et al. . |
| 5,141,500 | 8/1992 | Hake . |

FOREIGN PATENT DOCUMENTS

260312  4/1964  Australia ............................ 206/365

OTHER PUBLICATIONS

*Diabetes Forecast*, Jul. 1991, p. 28 (Advertisement for Prefilled Syringe Case).

Primary Examiner—Bryon P. Gehman
Attorney, Agent, or Firm—Quarles & Brady

[57] ABSTRACT

A container for transporting a syringe includes a tubular body and a tubular cap. The body has an open end to receive a syringe and that end has a pair of notches to receive and hold projections on the syringe so that movement of the syringe in the container is restricted. Threaded tabs extend longitudinally from the body in-between the notches and the cap threads onto the tabs to enclose the syringe. When the cap is tightened fully onto the body, the projections of the syringe are captured in the notches.

13 Claims, 1 Drawing Sheet

U.S. Patent    May 23, 1995    5,417,326
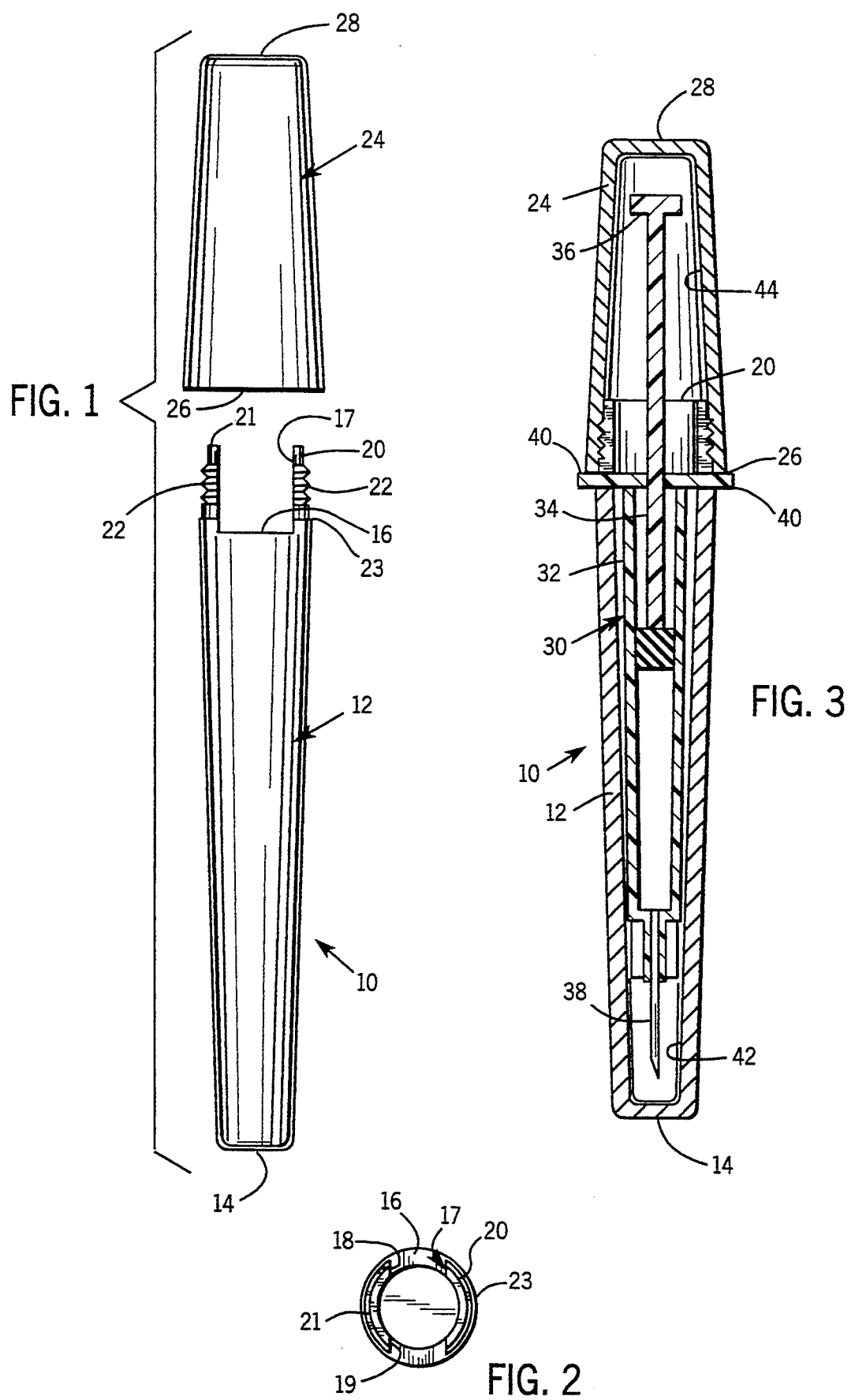

SYRINGE CONTAINER

BACKGROUND OF THE INVENTION

The present invention relates to containers for hypodermic syringes, and more particularly to containers that protect the syringe from damage, accidental discharge and from causing injury while being carried on a person.

Many medical patients must periodically self-administer medicine via a hypodermic injection. For example, diabetics periodically inject insulin into their bodies. If such patients are to lead relatively normal lives, they may be at a location that is remote from their home or work place at the time when the injection must occur. As a consequence, it is desirable for such patients and diabetics to carry a hypodermic syringe filled with medication on their person.

When a hypodermic syringe is carried in a pocket or a handbag, the syringe must be protected against breakage and other damage. In addition, the syringe must be safeguarded against accidental discharge and the needle protected from contamination.

SUMMARY OF THE INVENTION

The general object of the present invention is to provide a container for holding a hypodermic syringe and protect the syringe while being carried by a user.

Another object of the present invention is to provide a container that allows the syringe to be carried after being filled with a quantity of medicine to be injected.

A further object of the present invention is to design such a container that will hold the syringe in a manner which restricts syringe movement within the container. Such restriction safeguards the syringe from damage and prevents accidental discharge of a loaded syringe while in the container.

Yet another object is to provide a compact container that is carried easily in a pocket or purse.

These objectives are satisfied by a syringe container which comprises a tubular body and a tubular cap. The tubular body has first and second ends with an opening at the first end to receive a syringe. Notches extend into the body from the first end to receive projections on the syringe.

The cap has an opening at one end which abuts the first end of the body. A mechanism is provided to secure the cap to the body in a manner that captures the projections of the syringe in the notches. This capturing restricts movement of the syringe in the container.

In the preferred embodiment, two curved tabs are formed between the notches at the first end of the body. Each tab has threads on their external surfaces. The opening in the cap has internal threads which engage the threads on the tabs to attach the cap and the body. The cap preferably is sufficiently long to be able to receive a plunger of a syringe which is filled with medicine.

BRIEF DESCRIPTION OF THE DRAWINGS

FIG. 1 is an exploded view of a container according to the present invention;

FIG. 2 is a plane view of an open end of the body of the container; and

FIG. 3 is a longitudinal cross section through the container of FIG. 1 in a closed state with a syringe inside.

DESCRIPTION OF THE PREFERRED EMBODIMENT

With reference to FIG. 1, a container 10 for a syringe includes a tubular body 12 and a cap 24 which components of the container may be fabricated either of metal, a rigid plastic or other durable material. The body 12, which can be circular in cross-section, has a closed end 14 and an open end 16. The external surface of the tubular body 12 tapers inward from a larger diameter near the open end 16 to a smaller diameter at the closed end 14. A transverse channel 17 extends transversely across open end 16 and forms two curved tabs 20 and 21 projecting longitudinally from the open end of body 12. Threads 22 can be cut in the outer curved surfaces of each tab 20 and 21. The outer diameter of the tabs 20 and 21 is slightly less than the outer diameter of the body 12 at the closed end 16 thereby forming an external rim 23. As shown also in FIG. 2, the channel 17 forms notches 18 and 19 between the tabs 20 and 21 and the notches extend longitudinally into the body 12 past the rim 23.

The tubular cap 24, which can be circular in cross-section, has an open end 26 and a closed end 28. The cap 24 tapers from a larger diameter at the open end 26 to a smaller diameter at the closed end 28. The internal diameter of the cap's open end 26 is sized to receive the tabs 20 and 21 of body 12. Internal threads are cut in the open end 26 of the cap so that the cap may be threaded onto the tabs 20 and 21 of the body.

When the cap 24 is tightened fully onto the threaded tabs, the surface at the open end 26 of the cap abuts the rim 23 of the body 12. Because the notches 18 and 19 at the open end 16 of the body 12 extend longitudinally into the body beyond the rim 23, a small slot opening is formed on each side of the container when the cap abuts the rim. As will be described, these slot openings are adapted to receive projections on a syringe to restrict movement of the syringe placed in the container and facilitate construction of a smaller diameter container.

FIG. 3 illustrates the container 10 in a closed state with a hypodermic syringe 30 held therein. The syringe 30 has a conventional barrel 32 within which is located a plunger 34 with a thumb button 36 at one end thereof. The barrel 32 has a needle 38 projecting from one end and has projections 40 extending radially from opposite sides of the other end of the barrel 32. Such projections 40 commonly are found on disposable syringes, such as those used by diabetics to inject insulin. To inject the insulin, the user places the barrel between the forefinger and middle finger with the projections 40 abutting the fingers and then presses the thumb button 36 to push the plunger through the barrel, which causes insulin to flow from the barrel through the needle 38.

When the syringe 30 is placed into the container 10, the needle rests within the inner cavity 42 of the body adjacent the closed end 14. The projections 40 of the syringe barrel 32 fit within the channel notches 18 and 19 at the open end of the body 12, thus enabling the outer diameter of the container 10 to be smaller than if the projections 40 have to fit within inner cavity 42. As the cap 24 is tightened onto the body 12, the surface at the open end 26 of the cap pushes against the syringe projections 40 capturing them against the bottom of the notches 18 and 19 as illustrated. This engagement of the cap and body with the projections 40 holds the syringe 30 in a fixed position within the container 10. In addition, the inner diameter 42 of the body tapers from a relatively large diameter adjacent the open end 16 to a smaller diameter near closed end 14. This tapering provides an inner surface of cavity 42 that is slightly larger than the end of the barrel 32 at which the needle 38 is located, thereby preventing significant transverse movement of the syringe near the closed end 14 of the body.

This engagement of the syringe with the container holds the syringe safely therein. The container not only shields the syringe 30 from damage, the engagement with the container restricts the movement of the syringe, which movement also could damage the syringe.

The inner opening 44 within the cap 28 is sufficiently deep so that the container 10 is able to accommodate a syringe which has been filled with a medicine. In the filled state the plunger 34 extends from the barrel 32 with the button 36 projecting farther into the inner cap chamber 44 and lying closer to the closed end 28 of the cap 24. Thus the container safeguards a filled syringe against accidental discharge.

I claim:

1. A syringe container comprising:
    a tubular body having a first end, a second end and a wall forming an inner cavity between the first end and the second end, the first end having a first opening to receive a syringe, and a first notch, extending through said wall and from the first end, to receive a projection on a syringe; and
    a cap with a second opening and a mechanism securing said cap to the first end of said body in a manner that captures the projection on a contained syringe in the first notch.

2. The syringe container as recited in claim 1 wherein said body has a second notch extending through said wall and from the first end on an opposite side of the first opening from the first notch, said second notch for receiving another projection on a contained syringe which will be captured in the second notch by said cap.

3. The syringe container as recited in claim 2 wherein:
    said body further includes two curved tabs at the first end with the tabs being separated by the first and second notches, each tab having an external surface with threads thereon; and
    the second opening of said cap has internal threads for engaging the threads on the tabs of said body to attach said cap to said body.

4. The syringe container as recited in claim 2 wherein said body further includes two tabs formed at the first end between the notches with each tab having an element that engages said cap thereby preventing said cap from being pulled from said body.

5. The syringe container as recited in claim 1 wherein said cap has a cavity for receiving a plunger of a syringe with the cavity being of sufficient size to accommodate the plunger when the syringe is filled with medicine.

6. The syringe container as recited in claim 1 wherein said body has a circular cross section at all points between the first end and the second end.

7. A container for a syringe wherein the container comprises:
    a tubular body having an internal cavity, an open end and a closed end with a longitudinal axis between the open end and the closed end, said tubular body tapering inward from the open end to the closed end, and said tubular body has a pair of tabs projecting longitudinally from the open end to form a channel between the pair of tabs, which channel is transverse to the longitudinal axis and open at the two transverse ends to an external environment of said tubular body; and
    a tubular cap having an opening at one end for receiving the tabs of said tubular body to attach said clap to said tubular body in a manner which maintains the two transverse ends of the channel open to the external environment.

8. The container as recited in claim 7 wherein an external surface of each tab is threaded and the opening of said cap has internal threads for engaging the threads of the tabs.

9. The container as recited in claim 7 wherein the channel receives projections extending from a barrel of a syringe that is received in the open end of said tubular body and the cap holds the projections in the channel when the cap is attached to said tubular body.

10. An apparatus comprising:
    a body having a tubular wall forming an inner cavity with an open end, and having a pair of notches extending through the tubular wall and from the open end into said body;
    a syringe with a barrel located within the inner cavity of said tubular body and having two projections extending radially from one end of the barrel and into the notches in said tubular body, and a plunger within the barrel and extending from the open end of said tubular body; and
    a cap attached to the open end of said tubular body and extending around a portion of the plunger that extends from said tubular body, said cap capturing the projections on the barrel in the pair of notches.

11. The apparatus as recited in claim 10 wherein said tubular body further includes two tabs formed at the open end between the notches with each tab having an element that engages said cap thereby preventing said cap from being pulled from said body.

12. The apparatus as recited in claim 10 wherein:
    said tubular body further includes two curved tabs formed at the open end between the pair of notches with each tab having external threads; and
    said cap having a opening with internal threads that engage the external threads on the tabs of said tubular body.

13. The apparatus as recited in claim 10 wherein said cap has a cavity for receiving the plunger of the syringe with the cavity being of sufficient size to accommodate the plunger when the syringe is filled with medicine.

* * * * *